United States Patent
Lee et al.

(10) Patent No.: US 11,280,781 B2
(45) Date of Patent: Mar. 22, 2022

(54) APPARATUS AND METHOD FOR EXTRACTING GENOME USING ULTRASOUND TRANSDUCER AND MAGNETIC BEAD

(71) Applicant: KOREA INSTITUTE OF SCIENCE AND TECHNOLOGY, Seoul (KR)

(72) Inventors: Soo Hyun Lee, Seoul (KR); Nakwon Choi, Seoul (KR); Byung Chul Lee, Seoul (KR); Hyungbeen Lee, Seoul (KR); Mintack Oh, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/587,062

(22) Filed: Sep. 30, 2019

(65) Prior Publication Data
US 2020/0110082 A1    Apr. 9, 2020

(30) Foreign Application Priority Data
Oct. 4, 2018    (KR) .......................... 10-2018-0118414

(51) Int. Cl.
*G01N 33/543*    (2006.01)
*C12M 1/00*    (2006.01)
*G01N 29/02*    (2006.01)
*C12N 15/10*    (2006.01)

(52) U.S. Cl.
CPC ....... *G01N 33/54333* (2013.01); *C12M 29/00* (2013.01); *C12N 15/1003* (2013.01); *G01N 29/02* (2013.01)

(58) Field of Classification Search
CPC ........ G01N 33/54333; G01N 35/0098; G01N 29/02; B01F 11/0266; B01F 13/08; B01F 11/0283; C12N 15/1003; C12N 15/1013; C12N 29/00; C12Q 2523/301
See application file for complete search history.

(56) References Cited

U.S. PATENT DOCUMENTS

| | | | |
|---|---|---|---|
| 2009/0052272 A1 | 2/2009 | Sarvazyan | |
| 2010/0137575 A1* | 6/2010 | Connolly | C12Q 1/6806 536/25.41 |
| 2011/0028703 A1* | 2/2011 | Hollenstein | B01F 11/0266 536/23.1 |
| 2011/0137018 A1* | 6/2011 | Chang-Yen | G01N 35/0098 530/412 |
| 2014/0336083 A1* | 11/2014 | Khattak | B05D 3/002 506/39 |

FOREIGN PATENT DOCUMENTS

KR    1020170038974 A    4/2017

OTHER PUBLICATIONS

Bioneer Brochure, "His-tagged Protein Purification", 2014, 6 pages, English translation of relevant portions is attached.
(Continued)

*Primary Examiner* — Betty J Forman
(74) *Attorney, Agent, or Firm* — Cantor Colburn LLP

(57) ABSTRACT

The present disclosure relates to an apparatus and a method for extracting genome, capable of acquiring a sufficient amount of genome for genetic analysis with high extraction efficiency, even with a small amount of target sample.

9 Claims, 17 Drawing Sheets

(56) References Cited

OTHER PUBLICATIONS

Bioneer Brochure, MagListo TM, "Magnetic Bead-based Prep and Purification Solution", 2016, 16 pages.
Bioneer Brochure, Next Generation Magnetic Bead, AccuNanoBead TM, 2019, 8 pages.
Ida Iranmanesh et al., "Acoustic micro-vortexing of fluids, particles and cells in disposable microfluidic chips," Biomed Microdevices, Jul. 21, 2016, 7 pages.

* cited by examiner

FIG. 6C

| Method (blood volume) | Control1 (100 μl) | Control2 (5 μl) | Present disclosure (Quick) (5 μl) | Present disclosure (5 μl) | Present disclosure (10 μl) | Present disclosure (20 μl) | Present disclosure (40 μl) |
|---|---|---|---|---|---|---|---|
| Ct | 26.63 | 31.48 | 29.11 | 28.24 | 27.76 | 26.53 | 25.51 |
| Conc. (ng/μl) | 1.77 | 0.08 | 0.41 | 0.75 | 1.05 | 2.46 | 5.01 |

0.6 ~ 0.8 MHz 0.8 ~ 1.0 MHz 1.0 ~ 1.2 MHz 1.2 ~ 1.4 MHz

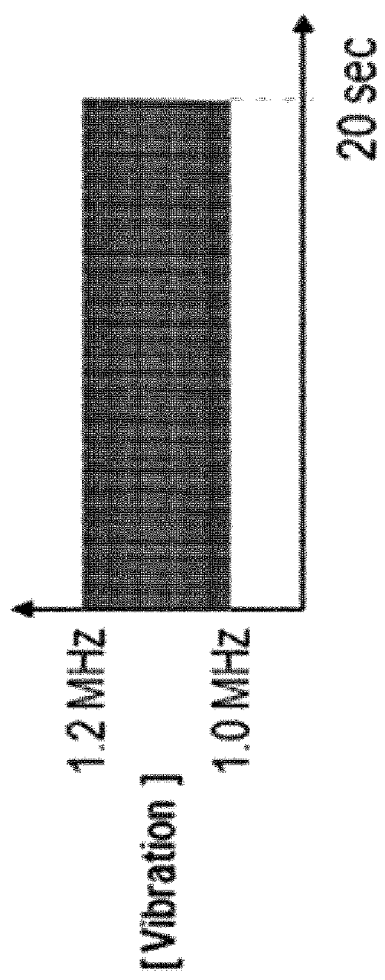

APPARATUS AND METHOD FOR EXTRACTING GENOME USING ULTRASOUND TRANSDUCER AND MAGNETIC BEAD

CROSS-REFERENCE TO RELATED APPLICATIONS

The present disclosure claims priority to Korean Patent Application No. 10-2018-0118414 in the Republic of Korea, the disclosures of which are incorporated herein by reference.

BACKGROUND

1. Field of the Invention

The present disclosure relates to an apparatus and a method for extracting genome using an ultrasound transducer and a magnetic bead.

2. Description of the Related Art

Diagnosis of disease of individuals through genetic analysis has been actively developed recently. In particular, recently, there has been a growing interest in personalized medication based on the metabolic genome of the individuals, which prescribes different doses of medicines in consideration of individual genetic differences.

Such genetic analysis is performed by collecting samples such as saliva and blood from individuals, and then extracting genomes such as DNA and RNA from the samples and analyzing the extracted genomes.

Since there are several factors other than the target genome that interfere with the amplification of the genome in the sample taken for genetic analysis, the process of extracting the pure target genome DNA and RNA from the sample, that is, the sample preprocessing process is essential for successful analysis.

Electroporation has been used as a method for extracting a target genome from a sample. While the electroporation has the advantage of being able to extract a target genome such as DNA or RNA by electrodissolution rather than cell lysis that uses chemicals, it also has the disadvantage of being able to extract the target genome only from the cell solution, and not able to extract the target genome from the blood.

Since the currently available kits for extracting the target genome from the blood need a long time to extract the target genome, and a large amount of blood to obtain the amount of genome required for genetic analysis in consideration of the deterioration of extraction efficiency due to the agglomeration of magnetic beads, there is a shortcoming that patient is discomforted during blood sampling. In addition, some kits have a considerable disadvantage in that the extraction is performed in a tube form rather than a chip form, which limits use thereof for the on-site diagnosis.

Therefore, there is a growing demand for apparatus and method for extracting genome, which can extract a sufficient amount of target genome for genetic analysis even with a small amount of blood.

PRIOR ART DOCUMENTS

Patent Literature

U.S. Published Patent Application No. 2009-0052272 (Feb. 26, 2009)

Korean Patent Publication No. 10-2017-0038974 (Apr. 10, 2017)

SUMMARY

The present disclosure relates to an apparatus and a method for extracting genome, capable of acquiring a sufficient amount of genome for genetic analysis with high extraction efficiency, even with a small amount of target sample.

According to an exemplary embodiment, a method for extracting genome is provided, which may include (a) introducing a solution containing a plurality of magnetic beads b into a channel 110, (b) moving a magnetic body 200 to a first position with respect to the channel 110 to cause agglomeration of the plurality of magnetic beads b, and discharging the solution excluding the plurality of magnetic beads b to outside of the channel 110, (c) introducing a solution containing a lysis buffer and a target sample into the channel 110, and (d) moving the magnetic body 200 to a second position with respect to the channel 110, and applying ultrasound energy of a predetermined pattern to the channel 110, in which the plurality of magnetic beads b are collided against a substance contained in the target sample so that the substance is lysed, and the target genome contained in the substance is eluted and adsorbed to the plurality of magnetic beads b, in which a distance between the magnetic body 200 and the channel 110 in the first position is shorter than in the second position.

In one embodiment, the method for extracting genome may further include, after step (d), (e) moving the magnetic body 200 to the first position to cause agglomeration of the plurality of magnetic beads b to which the target genome is adsorbed, discharging the solution excluding the plurality of magnetic beads b to which the target genome adsorbed to the outside of the channel 110, and introducing a washing buffer into the channel 110, (f) moving the magnetic body 200 to the second position and applying the ultrasound energy of the predetermined pattern to the channel 110.

In one embodiment, the method for extracting genome may further include, after step (f), (g) moving the magnetic body 200 to the first position to cause agglomeration of the plurality of magnetic beads b to which the target genome is adsorbed, discharging the solution excluding the plurality of magnetic beads b to which the target genome adsorbed to the outside of the channel 110, and introducing an elution solution for separating the target genome from the plurality of magnetic beads b into the channel 110, and (h) moving the magnetic body 200 to the second position and applying the ultrasound energy of the predetermined pattern to the channel 110.

In one embodiment, the predetermined pattern of the ultrasound energy may include a first pattern having a predetermined voltage for a predetermined first time period, in which frequency linearly increases from a first frequency to a second frequency, after the first pattern, a second pattern having the predetermined voltage for the predetermined first time period, in which the frequency linearly decreases from the second frequency to the first frequency, a third pattern having the predetermined voltage for a predetermined second time period, in which ultrasound energy is not applied, after the third pattern, a fourth pattern having the predetermined voltage for the predetermined first time period, in which the frequency linearly increases from the first frequency to the second frequency, after the fourth pattern, a fifth pattern having the predetermined voltage for the predetermined first time period, in which the frequency linearly decreases from the second frequency to the first frequency, in which the second frequency may be higher than the first frequency, and the first time period may be shorter than the second time period.

In one embodiment, when the predetermined pattern includes the first pattern, the second pattern, the fourth pattern and the fifth pattern, the magnetic body 200 may be located in the second position, and when the predetermined pattern is the third pattern, the magnetic body 200 may be located in the first position.

In one embodiment, the ultrasound energy of the predetermined pattern may be applied to the channel 110 for a predetermined number of times or more in the steps (d), (h), and (f).

In one embodiment, after step (h), the method may further include a step of (i) moving the magnetic body 200 to the first position to cause agglomeration of the plurality of magnetic beads b.

In one embodiment, the target sample may be blood.

In one embodiment, the substance that collides with the plurality of magnetic beads b may be leukocyte, and the target genome may be DNA or RNA.

In one embodiment, the first frequency may be in the range of 0.95 MHz to 1.05 MHz, the second frequency may be in the range of 1.14 MHz to 1.26 MHz, and the predetermined voltage may be in the range of 270 mV to 330 mV.

In one embodiment, the predetermined first time period may be in the range of 9 to 11 seconds, and the predetermined second time period may be in the range of 36 to 44 seconds.

The present disclosure provides an apparatus for extracting genome for carrying out the method described above, in which the apparatus may include a chip 100 having an in-let 111 and an out-let 115, and a channel 110 formed between the in-let 111 and the out-let 115, in which the target genome is extracted in the channel 110, a magnetic body 200 that moves between the first position and the second position to cause agglomeration of the plurality of magnetic beads b accommodated in the channel 110, and an ultrasound transducer 300 for applying the ultrasound energy of the predetermined pattern to the chip 100.

In one embodiment, the apparatus for extracting genome may further include a tube 400 connected to the out-let 115 to discharge the fluid accommodated in the channel 110.

In one embodiment, the apparatus for extracting genome may further include a driving device 500 electrically connected to the magnetic body 200 to control a movement of the magnetic body 200, a function generator 600 for generating an electric signal of a predetermined pattern of the ultrasound energy applied by the ultrasound transducer 300, and an amplifier 700 for amplifying the electric signal generated by the function generator 600.

The present disclosure as described above has the following effects.

Since the target genome is extracted with a high extraction efficiency, a sufficient amount of DNA can be extracted for genetic analysis even with a small amount of blood sample, and pain experienced by the patient during blood sampling is minimized compared to the conventional apparatuses that require large amounts of blood. In particular, since it is possible to extract DNA with high efficiency so that genetic analysis can be performed even with only the amount of blood acquired by pricking a finger or the like with a needle, the present disclosure is very simple and cost-effective as compared to the conventional cases that extract a blood sample from a vein using a needle.

In addition to high extraction efficiency, the present disclosure can extract DNA in a relatively short time as compared with the related DNA extraction apparatus, and thus is suitable for on-site diagnosis. Further, DNA can be extracted from the blood by simple apparatuses and methods without requiring professional personnel or professional equipment, which is also suitable for on-site diagnosis.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 6A to 6C show experimental results of Verification Experiment 2 for verifying superiority by using the apparatus and the method for extracting genome according to an embodiment of the present disclosure;

FIG. 8A to 8D show experimental results of the Verification Experiment 4 for verifying the superiority of ultrasound energy of a predetermined pattern applied to the chip 100 by using the apparatus and the method for extracting genome according to an embodiment of the present disclosure.

DETAILED DESCRIPTION

Hereinafter, the present disclosure will be described in detail with reference to the accompanying drawings.

1. Apparatus for Extracting Genome

Figure 1:
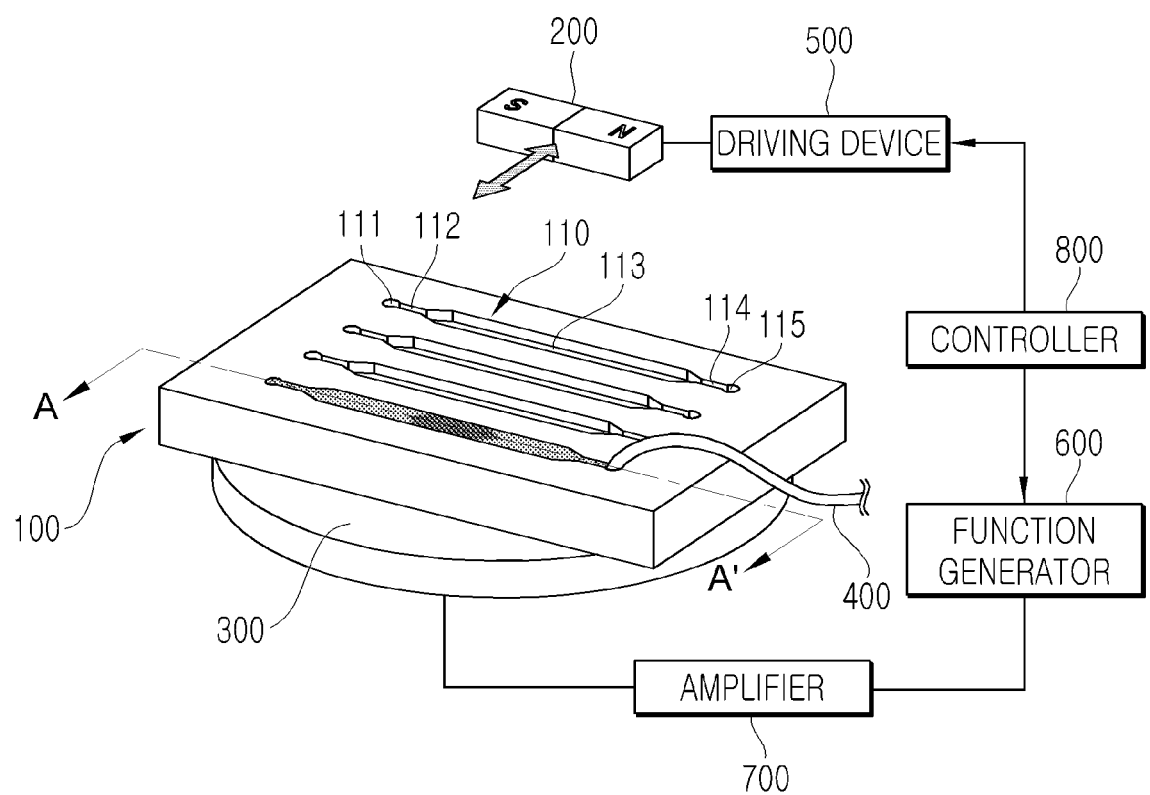
FIG. 1 is a schematic view provided to explain an apparatus for extracting genome according to an embodiment of the present disclosure.

An apparatus for extracting genome according to an embodiment of the present disclosure will be described in detail with reference to FIG. 1. FIG. 1 is a schematic diagram showing the apparatus for extracting genome according to an embodiment of the present disclosure.

Referring to FIG. 1, the apparatus for extracting genome includes a chip 100, a magnetic body 200, an ultrasound transducer 300, a tube 400, a driving device 500, a function generator 600, an amplifier 700, and a controller 800.

The chip 100 includes one or more channels 110 having an in-let 111 and an out-let 115. The channel 110 includes the in-let 111, a passage channel 112, a reaction channel 113, a discharge channel 114, and the out-let 115.

More specifically, as shown in FIG. 1, the channel 110 includes the circular in-let 111 having a predetermined diameter, the passage channel 112 which has a width smaller than the diameter of the in-let 111 and through which the fluid introduced into the in-let 111 passes, the reaction channel 113 which has a width larger than the width of the passage channel 112 and through which genome is extracted from an introduced target sample, the discharge channel 114 through which the fluid in the reaction channel 113 passes to be discharged to the outside, and the circular out-let 115 connected to the tube 400 to allow the fluid to be discharged to the outside. Here, the shapes of the in-let 111 and the out-let 115 may be the same as each other, and the shapes of the passage channel 112 and the discharge channel 114 may also be the same as each other.

Such channel 110 is preferably a micro fluidic channel, and an amount of fluid that can be accommodated by the channel 110 may be from 90 µl to 110 µl, or more specifically, 100 µl, although not limited thereto.

A solution containing magnetic beads b is introduced into the channel 110 through the in-let 111, and the magnetic beads b are agglomerated using the magnetic body 200 described below, and the solution excluding the magnetic beads b is discharged to the outside through the out-let 115 and the tube 400, and then a solution containing the target sample can be introduced through the in-let 111. The surfaces of the magnetic beads b have a positive charge (+) so that a target genome, that is, DNA or RNA having a negative charge (−) can be adsorbed to the surfaces of the magnetic beads b. This will be described in greater detail below.

The magnetic body 200 may be an object having magnetism, such as a permanent magnet or an electromagnet. The magnetic body 200 is electrically connected to the driving device 500 to be moved back and forth by the driving device 500. At this time, it is defined that the magnetic body 200 and the chip 100 are at the shortest distance to each other in a first position (that is, in a position where the magnetic body 200 is disposed directly above the chip 100), and are at the longest distance to each other in a second position (that is, in a position at which the magnetic force of the magnetic body 200 hardly acts on the channels 110 of the chip 100).

Figure 2A:
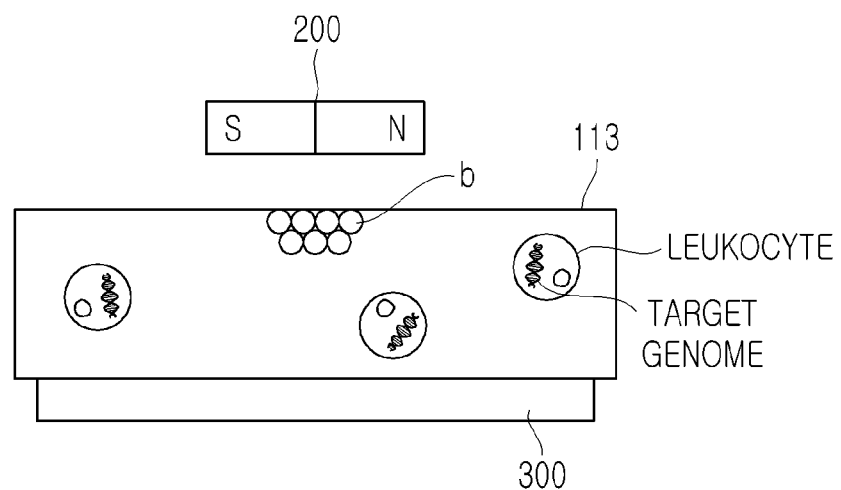
FIGS. 2A to 2D are cross-sectional views taken along the line A-A' in FIG. 1, illustrating a process of extracting a target genome by using the apparatus for extracting genome of FIG. 1.
Figure 2B:
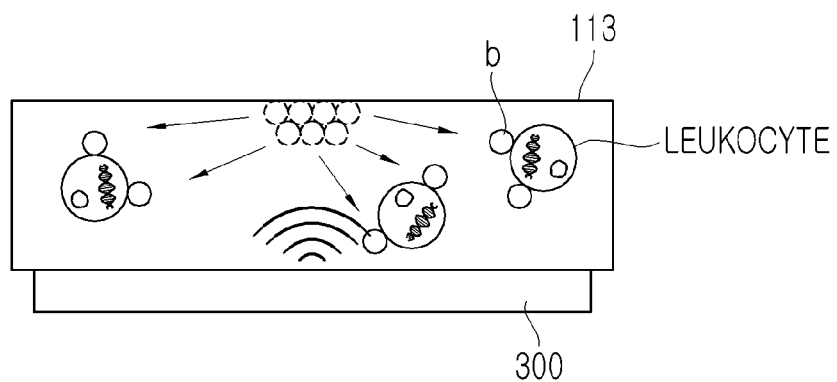
Figure 2C:
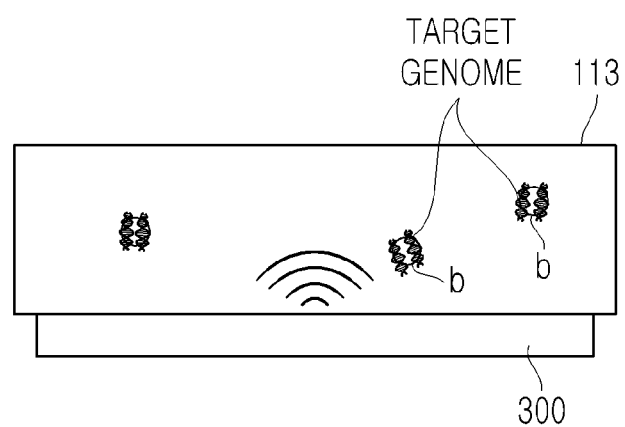

The magnetic force generated by the magnetic body 200 strongly acts on the channels 110 in the first position, causing agglomeration of the magnetic beads b accommodated in the channels 110 (see FIG. 2A), and the magnetic force generated by the magnetic body 200 hardly acts on the channels 110 in the second position and the magnetic beads b accommodated in the channels 110 are dispersed (see FIG. 2B).

The ultrasound transducer 300 is located below the chip 100 to apply ultrasound energy of a predetermined pattern to the chip 100. First, the function generator 600 generates an electric signal of a predetermined pattern, the amplifier 700 amplifies the electric signal generated by the function generator 600, and the amplified electric signal is converted into physical ultrasound energy by the ultrasound transducer 300. The ultrasound energy converted by the ultrasound transducer 300 is applied to the chip 100 and causes vibrations of the magnetic beads b accommodated in the channels 110. The magnetic beads b vibrating in the channels 110 collide against the substance contained in the target sample, and with the lysis of the substance, the target genome contained in the substance is adsorbed to the magnetic beads b.

Here, the function generator 600 generates an electric signal having a predetermined pattern, and since the electric signal is generated with the predetermined pattern rather than a constant magnitude, the extraction efficiency of the target genome is greatly enhanced. This will be described in greater detail below.

The tube 400 is connected to the out-let 115 of the channel 110 and the fluid accommodated in the channel 110 is discharged therethrough. Although not shown in the drawings, the other end of the tube 400 may be connected to a waste liquid chamber and the solution discharged through the tube 400 may be introduced into the waste liquid chamber.

The driving device 500 is connected to the magnetic body 200 to control the movement of the magnetic body 200. Specifically, the driving device 500 moves the magnetic body 200 between the first position and the second position, and is not limited to any specific form as long as it is capable of controlling the movement of the magnetic body 200.

The controller 800 is electrically connected to the driving device 500 and the function generator 600 to control the operations thereof. As will be described below, the operations of the driving device 500 and the function generator 600 continuously change over time, and the controller 800 controls the driving device 500 and the function generator 600 to be operated in a predetermined order.

2. Method for Extracting Genome

Next, a method for extracting genome according to an embodiment of the present disclosure will be described in more detail with reference to FIGS. 2A to 2D, 3, and 4.

First, a solution containing a plurality of magnetic beads b corresponding to a capacity of the channel 110 is introduced through the in-let 111 of the channel 110 (S100). However, it is needless to say that a solution having a capacity smaller or greater than the capacity of the channel 110 can also be introduced into the channel 110.

Next, the driving device 500 moves the magnetic body 200 to the first position, and the plurality of magnetic beads b accommodated in the channel 110 is agglomerated (S110).

Next, with the magnetic body 200 still held in the first position, the solution accommodated in the channel 110 is discharged to the outside through the out-let 115 and the tube 400 (S120). A method (defined herein as "air washing") applicable in this step includes placing a pipette at the in-let 111, and pressing a handle of the pipette, according to which the inner air is introduced into the channel 110, pushing the solution to the outside through the out-let 115. Since the magnetic beads b are influenced by the magnetic force of the magnetic body 200, the magnetic beads b are not discharged to the outside, but held in the agglomerated state.

Next, with the magnetic body 200 still held in the first position, a lysis buffer, a target sample (e.g., blood), and a solution mixing a proteolytic enzyme (e.g., Proteinase K) solution and isopropyl alcohol (IPA) is introduced by an amount corresponding to the capacity of the channel 110 through the inlet 111 (S200). When blood is the target sample, the state shown in FIG. 2A will appear after this step is performed.

Next, the driving device 500 moves the magnetic body 200 to the second position so that a plurality of beads b are dispersed, the function generator 600 generates an electric signal of a predetermined pattern, the generated electric signal is converted into ultrasound energy by the ultrasound transducer 300 through the amplifier 700, and this converted ultrasound energy is transmitted to the chip 100 to vibrate the beads b (FIG. 2B and S210). The substance (e.g., leukocyte) contained in the target sample is lysed not only by the lysis buffer, but also the physical impact due to vibration of the beads b, resulting in elution of the target genome contained therein (S220).

Here, since the plurality of magnetic beads b are initially in an agglomerated state before dispersing and vibrating, a greater impact can be exerted to the substance than when the beads b are initially in a dispersed state before vibrating, and it enables more effective lysis.

Next, the eluted target genomes are adsorbed to the magnetic beads b (S230). The surface of the magnetic beads b coated with silica or the like has a positive charge (+), and the DNA, RNA, and the like, which is the target genome, has a negative charge (−) so that they are adsorbed to each other by attraction force. However, any method may be applied as long as the magnetic beads b can specifically bind to and capture DNA and RNA which is the target genome.

Here, since the magnetic beads b continue to vibrate due to the ultrasound energy applied by the ultrasound transducer 300, the number of times of collision between the magnetic beads b and the target genome increases, and as a result, the adsorption of the target genome can be performed effectively.

Figure 2D:
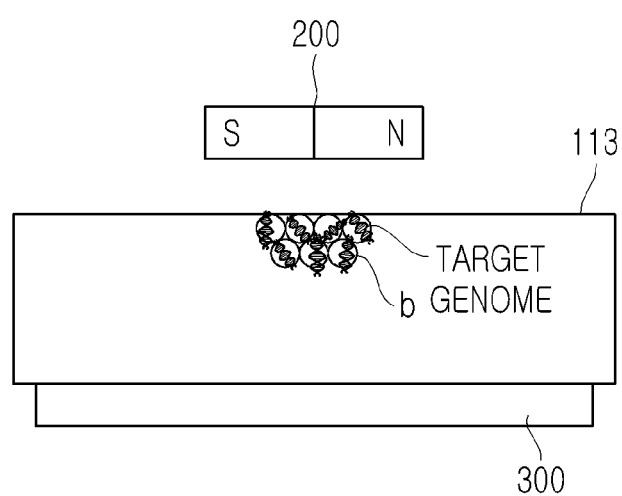

Next, as the driving device 500 moves the magnetic body 200 to the first position, the plurality of magnetic beads b adsorbed by the target genome are agglomerated (FIG. 2D and S240).

Next, with the magnetic body 200 still held in the first position, the solution accommodated in the channel 110 is discharged to the outside through the out-let 115 and the tube 400 (S250). This can be achieved by the air washing method described above, and since the magnetic beads b are influenced by the magnetic force of the magnetic body 200, the magnetic beads b are not discharged to the outside, but held in the agglomerated state.

Next, a washing buffer having a capacity greater than the capacity of the channel 110 is introduced into the channel 110 through the in-let 111 (S300). However, it is needless to say that a washing buffer having a capacity equal to or greater than the capacity of the channel 110 can also be introduced into the channel 110.

Next, the driving device 500 moves the magnetic body 200 to the second position, the ultrasound energy of the predetermined pattern in S500 is applied to the channel 110, and the substance excluding the target genome is washed and removed from the magnetic beads b (S310).

Next, the driving device 500 moves the magnetic body 200 to the first position, and accordingly, the plurality of magnetic beads b are agglomerated. Next, with the magnetic body 200 still held in the first position, the washing buffer accommodated in the channel 110 is discharged to the outside through the out-let 115 and the tube 400 (S320). This can be achieved by the air washing method described above, and since the magnetic beads b are influenced by the magnetic force of the magnetic body 200, the magnetic beads b are not discharged to the outside, but held in the agglomerated state.

Next, the above process (S310 and S320) is repeated once again so that the washing buffer is introduced into the channel 110 through the in-let 111, the magnetic body 200 is moved to the second position, ultrasound energy of a predetermined pattern is applied to the channel 110, the magnetic body 200 is moved to the first position, and the washing buffer accommodated in the channel 110 is discharged to the outside. Therefore, only the magnetic beads b adsorbed by the target sample remain in the channel 110, and the target genome is acquired with higher purity.

Next, an elution solution for separating the adsorbed target genome from the magnetic beads b is introduced through the in-let 111 by an amount corresponding to the capacity of the channel 110 (S400).

Next, the driving device 500 moves the magnetic body 200 to the second position, the function generator 600 generates an electric signal of a predetermined pattern, the generated electric signal is converted into ultrasound energy by the ultrasound transducer 300 through the amplifier 700, and the ultrasound energy is applied to the chip 100 to facilitate the separation of the target genome and the magnetic beads b (S410). The separation of the adsorbed target genome on the magnetic beads b is possible by introducing the elution solution alone, but this process may be facilitated more effectively by the application of the ultrasound energy. It is preferable that the process of magnetic bead b agglomeration, magnetic bead b dispersion followed by the ultrasonic energy application, and then magnetic bead b agglomeration is repeated, so that the target genome can be sufficiently separated from the magnetic beads b.

Finally, the tube 400 is separated from the chip 100 and a solution containing the target genome by the amount of necessary for the genetic analysis of the channel 110 is extracted through the out-let 115 (S500).

According to the method for extracting genome of the embodiment of the present disclosure, ultrasound energy of a predetermined pattern is applied to the chip 100.

Here, the predetermined pattern may be the pattern shown in FIG. 3, which will be described in detail below.

The predetermined pattern includes a first pattern having a predetermined voltage for a predetermined first time period, in which frequency linearly increases from a first frequency to a second frequency, a second pattern having the predetermined voltage for the predetermined first time period, in which frequency linearly decreases from the second frequency to the first frequency, a third pattern having the predetermined voltage for a predetermined second time period, in which ultrasound energy is not applied, a fourth pattern having the predetermined voltage for the predetermined first time period, in which frequency linearly increases from the first frequency to the second frequency, and a fifth pattern having the predetermined voltage for the predetermined first time period, in which frequency linearly decreases from the second frequency to the first frequency.

Here, the first frequency $f_1$ may be 0.95 MHz to 1.05 MHz, and more specifically, may be 1 MHz. Further, the second frequency $f_2$ may be 1.14 MHz to 1.26 MHz, and more specifically, may be 1.2 MHz.

Further, the predetermined voltage may be 270 mV to 330 mV, and more specifically, may be 300 mV.

Further, the predetermined first time period may be 9 to 11 seconds, and more specifically, may be 10 seconds, and the predetermined second time period may be 36 to 44 seconds, and more specifically, may be 40 seconds.

Here, when the ultrasound energy applied to the chip 100 has the third pattern, it is preferable that the driving device 500 moves the magnetic body 200 to the first position to cause agglomeration of the magnetic beads b, and when the ultrasound energy applied to the chip 100 has the first, second, fourth and fifth patterns, the driving device 500 moves the magnetic body 200 to the second position to enhance the efficiency of lysis. That is, during the time period when the ultrasound energy is not applied to the chip 100, the magnetic beads b are agglomerated by using the magnetic body 200, so that the magnetic beads b are in the agglomerated state by the time point when the magnetic beads b start to vibrate, which increases the amount of impact exerted on the substance contained in the target sample and thus results in more effective lysis.

It is preferable that the predetermined pattern described above is repeated for a predetermined number of times or more to ensure complete lysis of the substance contained in the target sample. The predetermined number of times is not limited, but may be three, for example.

In other words, a method for extracting genome according to an embodiment of the present disclosure properly disperses the magnetic beads b without agglomerating them due to the predetermined ultrasound pattern in the lysis step, thereby maximizing the effective surface area of the magnetic beads b so that as many target genome as possible can be attached to the magnetic beads b.

Further, the washing step enables the magnetic beads b to be properly dispersed by the predetermined ultrasound pattern, thereby preventing foreign materials and impurities from being caught between the magnetic beads b, and thus, it is possible to obtain a sample with high purity.

Further, in the elution step, it is easy to separate the target genome which is attached to the magnetic beads b by the predetermined pattern.

3. Verification Experiment 1

The verification experiment was conducted to verify the superiority of the apparatus for extracting genome according to the embodiment of the present disclosure (FIG. 5A to 5D).

First, the out-let 115 of the channel 110 is connected to the tube 400, and the waste liquid chamber is connected to the other end of the tube 400 to allow the solution discharged through the tube 400 to be introduced into the waste liquid chamber.

Then, 100 μl of a solution containing a plurality of magnetic beads b having a diameter of 4.6 μm was introduced into the channel 110 through the in-let 111.

Next, after the driving device 500 moved the magnetic body 200 to the first position to cause agglomeration of the magnetic beads b, the solution accommodated in the channel 110 was air-washed by using a pipette, and as a result, only a plurality of magnetic beads b agglomerated by the magnetic body 200 remained in the channel 110.

Next, with the magnetic body 200 still in the first position, 100 μl of a solution mixing lysis buffer:blood:a Proteinase K solution at a ratio of 7:7:1 and 40% isopropyl alcohol (IPA) was introduced into the channel 110 through the in-let 111.

Figure 3:
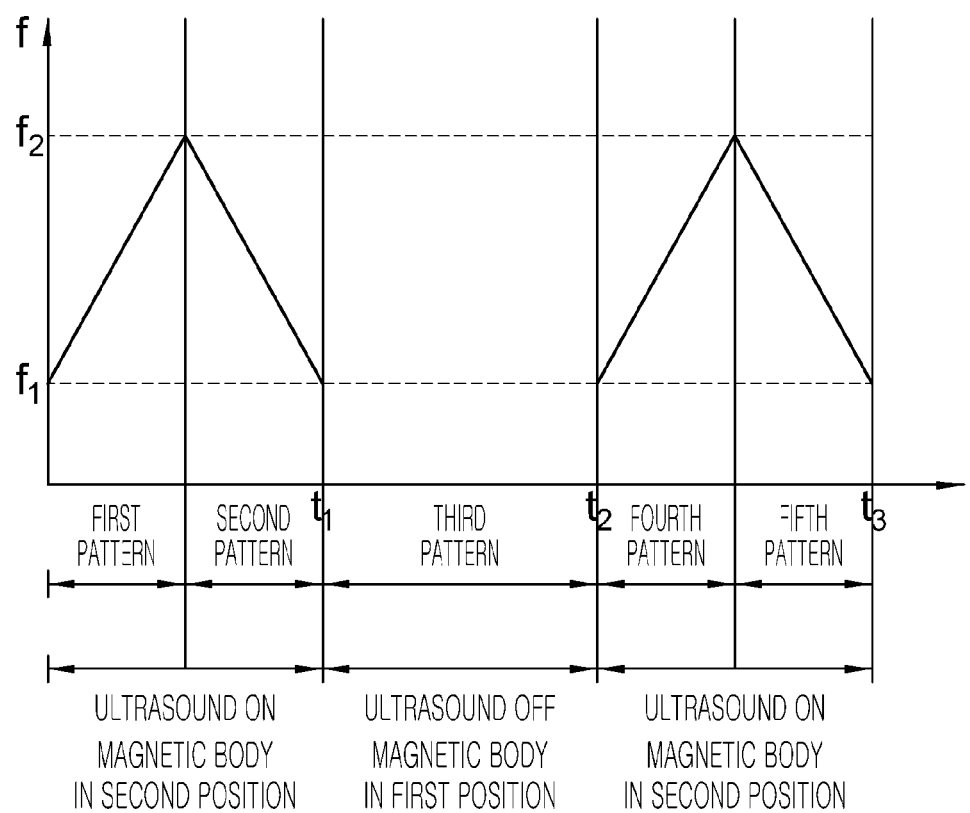
FIG. 3 is a view provided to explain a pattern of ultrasound energy transmitted to a chip 100 by the ultrasound transducer 300 of FIG. 1.
Figure 4:
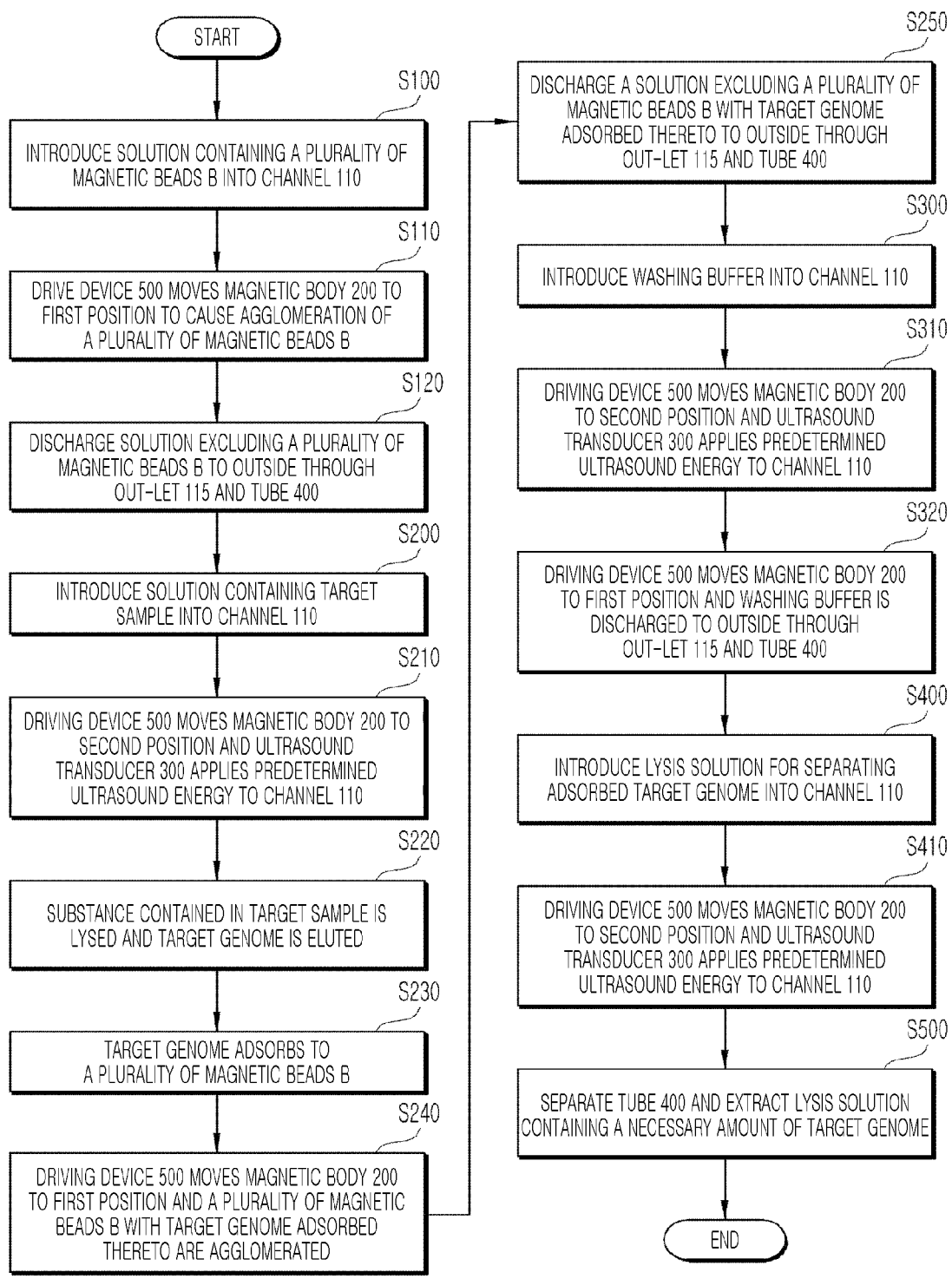
FIG. 4 is a flowchart provided to explain a method for extracting genome according to an embodiment of the present disclosure.

Next, the function generator 600 generated an electric signal corresponding to the pattern shown in FIG. 3, the electric signal was amplified through the amplifier 700, and the ultrasound transducer 300 converted the amplified electric signal into an ultrasound energy to vibrate the magnetic beads b, and as a result, leukocyte in the channel 110 were lysed and DNA in the leukocyte was adsorbed onto the magnetic beads b. This pattern was repeated three times.

Next, after the driving device 500 moved the magnetic body 200 to the first position to cause agglomeration of the magnetic beads b to which DNA is adsorbed, the solution accommodated in the channel 110 was air-washed, and as a result, only a plurality of magnetic beads b and DNA adsorbed thereto remained in the channel 110.

Next, with the magnetic body 200 still in the first position, 105 μl of washing buffer is introduced through the in-let 111 to discharge the substance un-adsorbed to the magnetic beads b through the tube 400 to the waste liquid chamber.

Next, the function generator 600 generated an electric signal corresponding to the pattern shown in FIG. 3, and after the driving device 500 moved the magnetic body 200 to the first position to cause agglomeration of the magnetic beads b to which DNA is adsorbed, the solution accommodated in the channel 110 was air-washed.

Next, with the magnetic body 200 still in the first position, 105 μl of washing buffer is introduced through the in-let 111 to discharge the substance un-adsorbed to the magnetic beads b through the tube 400 to the waste liquid chamber.

Next, the function generator 600 generated an electric signal corresponding to the pattern shown in FIG. 3, and after the driving device 500 moved the magnetic body 200 to the first position to cause agglomeration of the magnetic beads b to which DNA is adsorbed, the solution accommodated in the channel 110 was air-washed.

Next, with the magnetic body 200 still in the first position, 100 μl of the elution solution was introduced through the in-let 111, and the function generator 600 generated an electric signal corresponding to the pattern shown in FIG. 3 so that DNA was separated from the magnetic beads b. This pattern was repeated three times.

Next, the tube 400 was separated from the chip 100, and the elution solution with DNA extract was withdrawn through the out-let 115 and transferred to a 1.5 ml tube.

The apparatus for extracting genome according to the embodiment of the present disclosure was compared with the commercially available DNA extraction kits of DNA DIRECT™ Blood Kit (Control 1) and ChipGenie® edition P (Control 2) that extracts DNA by using magnetic beads and magnetic body only, to compare the DNA extraction efficiencies.

100 μl of blood was used in Control 1, and 46.67 μl of blood was used in both Control 2 and the apparatus for extracting genome according to the present disclosure. The result revealed that, while the DNA was extracted with 5% efficiency in Controls 1 and 2, the apparatus for extracting genome according to the present disclosure extracted the DNA with 11% efficiency, thus verifying the superiority of the present disclosure that is capable of extracting sufficient amount of DNA for genetic analysis even with a relatively small amount of blood (see FIG. 5C).

Figure 5A:
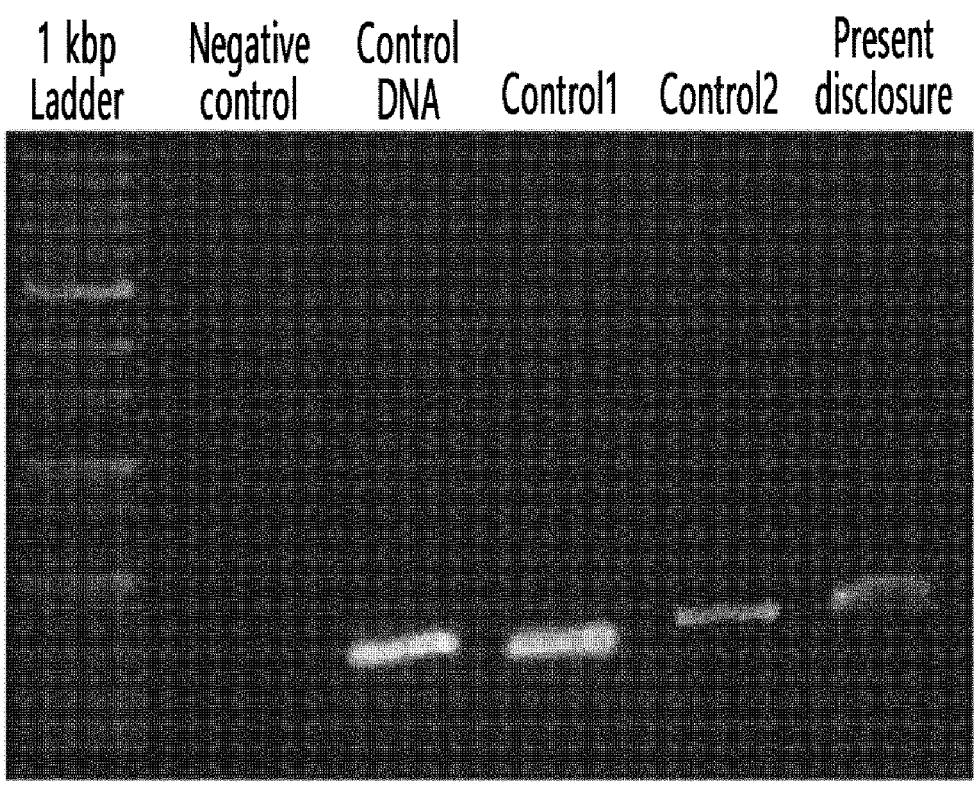
FIG. 5A to 5D show experimental results of Verification Experiment 1 for verifying superiority by using the apparatus and the method for extracting genome according to an embodiment of the present disclosure.
Figure 5B:
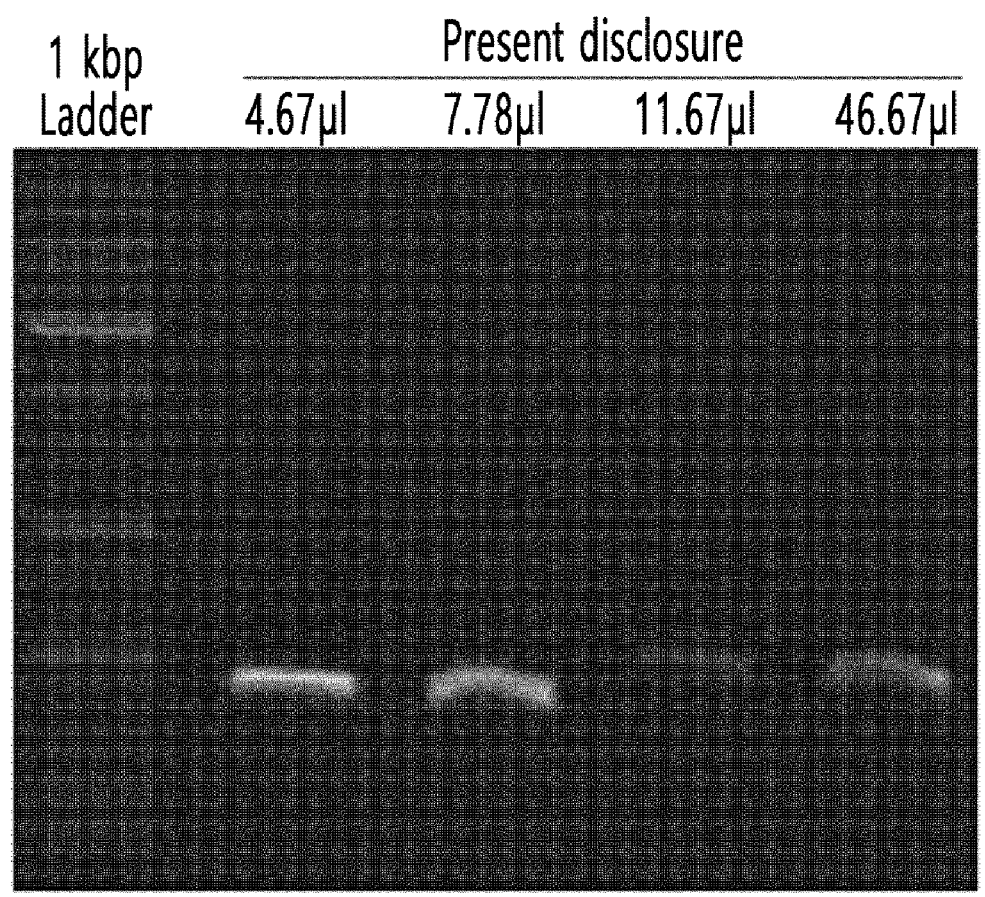
Figure 5C:
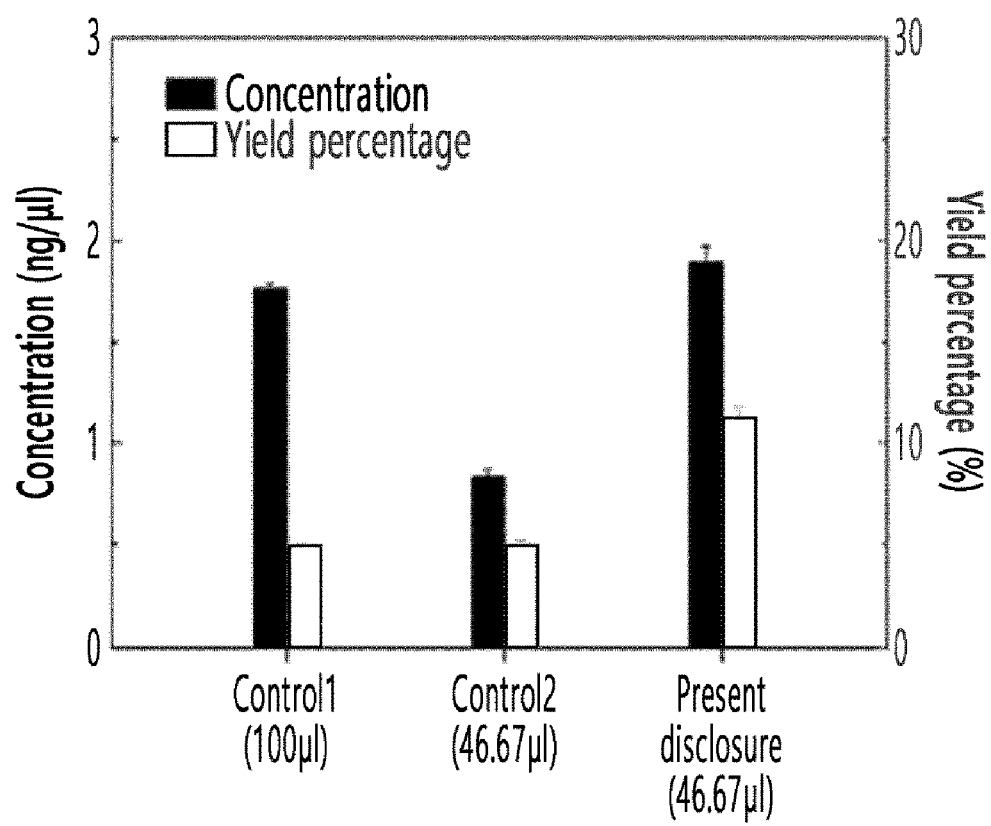
Figure 5D:
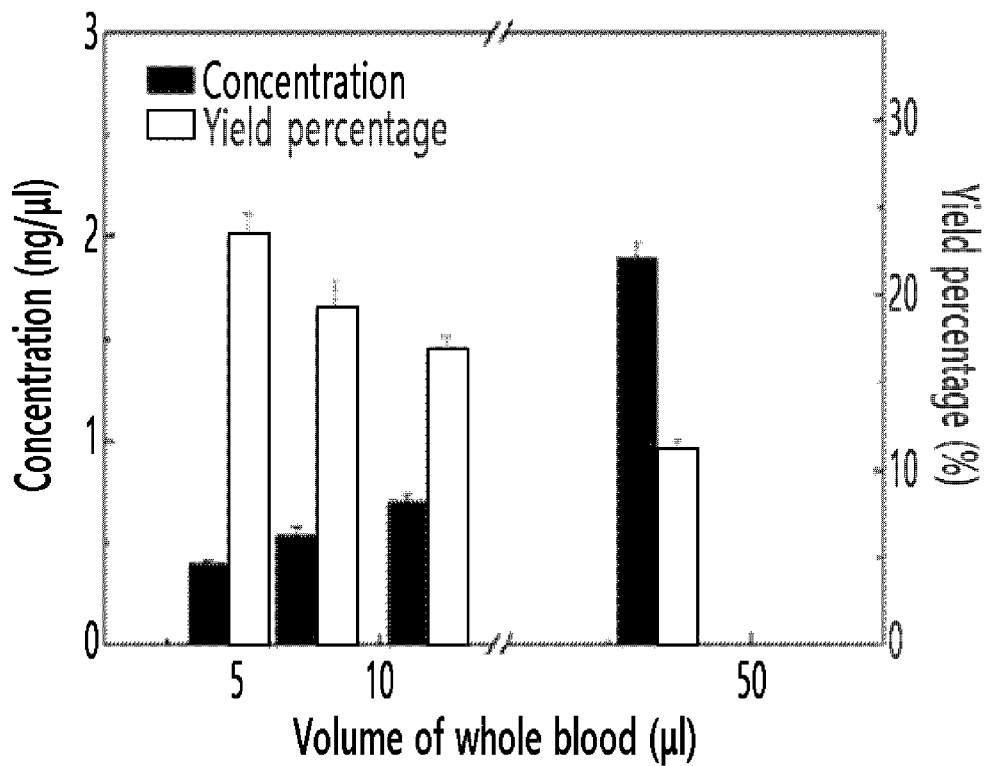

Further, as a result of measuring the DNA extraction efficiency while adjusting the amount of blood introduced into the channel 110 in the apparatus for extracting genome according to the present disclosure, it was confirmed that the highest extraction efficiency (about 25%) was achieved when 5 μl of blood was introduced, and the extraction efficiency decreased as the amount of blood increased (see FIG. 5D).

Verification Experiment 1 confirmed that the apparatus for extracting genome according to the present disclosure can extract DNA with high efficiency as compared with the other commercially available DNA extraction apparatuses, and also confirmed that the highest efficiency was achieved when about 5 μl of blood was introduced into the extraction device, thus solving the disadvantage of the related DNA extraction device that caused inconvenience of the patient by requiring a large amount of blood from the patient.

4. Verification Experiment 2

The verification experiment was conducted to verify the superiority of the apparatus for extracting genome according to the embodiment of the present disclosure.

Figure 6A:
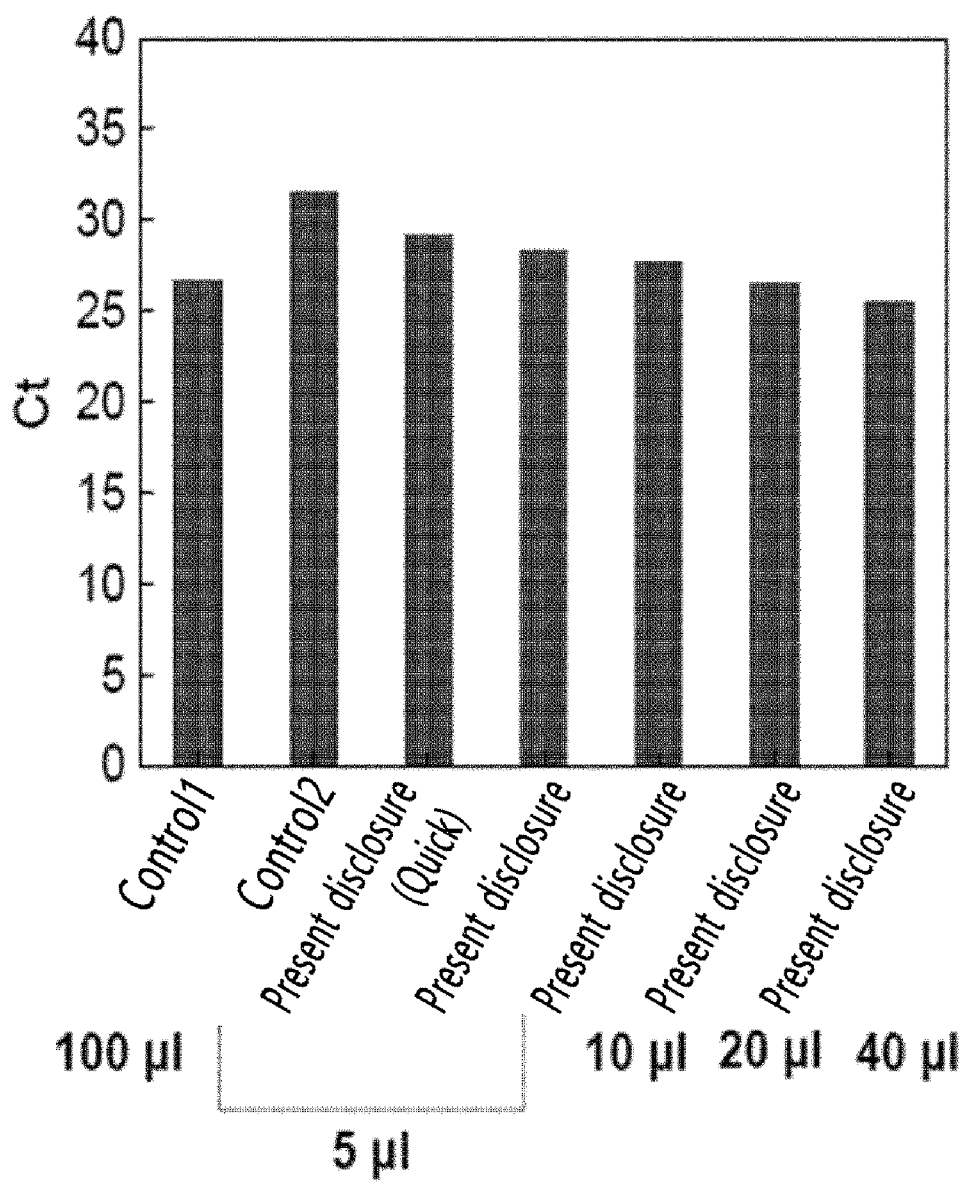
Figure 6B:
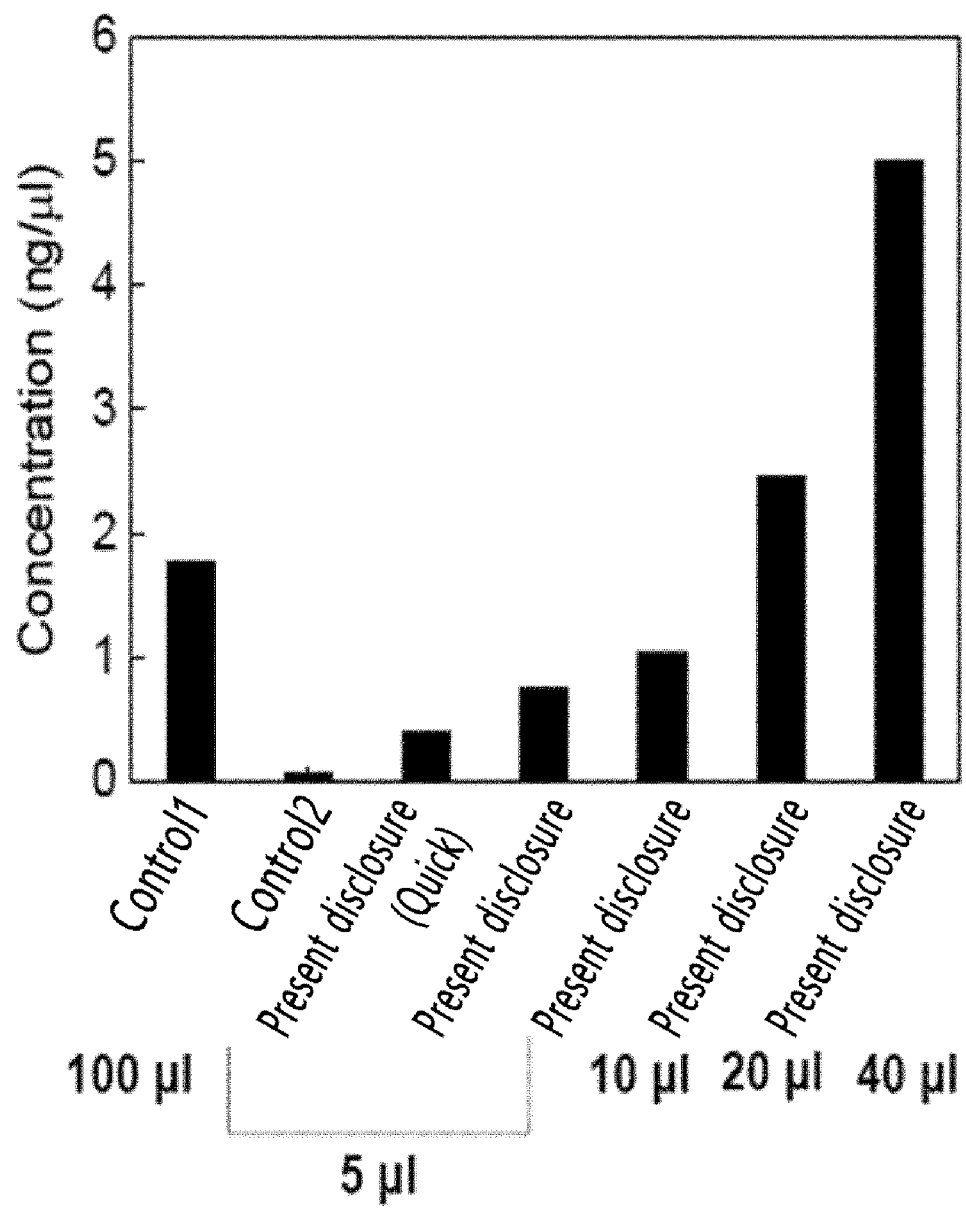

The apparatus for extracting genome according to the present disclosure was compared with the controls used in Verification Experiment 1, i.e., DNA DIRECT™ Blood Kit (Control 1) and ChipGenie® edition P (Control 2) that extracts DNA by using magnetic beads and magnetic body only, to compare the DNA extraction efficiencies (FIG. 6A to 6C).

In conducting the experiment, 100 μl of blood was used in Control 1, 5 μl of blood was used in Control 2, and 5 μl, 10 μl, 20 μl and 40 μl of blood was used in the apparatus for extracting genome according to the present disclosure. 'Quick' indicates a method for extracting genome according to the present disclosure, which is speeded up by minimizing the DNA extraction time by minimizing the washing step, or the like.

The result of the experiment was same as the result shown in FIG. 6A to 6C.

DNA extracted from blood is amplified by polymerase chain reaction (PCR), and in this amplification process, 'Ct' represents the number of cycles of PCR necessary for the amplified DNA to include the fluorescent substance and exhibit a predetermined fluorescence intensity. When there are more extracted DNAs, it is more likely that the predetermined fluorescence intensity can be exhibited with a small number of cycles. Thus, a smaller Ct value means a greater extraction efficiency.

While the result of the experiment indicated a Ct value of about 26 in Control 1, this cannot be considered to be a high extraction efficiency when considering 100 µl of blood was introduced, and when compared with Control 2, the apparatus for extracting genome according to the present disclosure showed a significant difference in the extraction efficiency. In addition, while it was confirmed that the Ct value decreased as the amount of blood increased, when considering the amount of blood introduced, it was confirmed that a high extraction efficiency was achieved when 5 µl of blood was introduced (FIGS. 6A and 6B).

In addition, as a result of extracting 100 µl of the elution solution from the channel 110 after the DNA extraction was completed and measuring and comparing the amount of DNA contained therein, it was confirmed that about 5 times more DNA than Control 2 was extracted even by the 'Quick' method that minimizes the washing step or the like, and when the method for extracting genome according to the present disclosure is applied, it was confirmed that about 9 times more DNA than Control 2 was extracted (FIG. 6C).

5. Verification Experiment 3

The verification experiment was conducted to find the optimum frequency bandwidth of ultrasound energy transmitted to the chip 100 by the ultrasound transducer 300 (FIG. 7A to 7D).

First, the out-let 115 of the channel 110 is connected to the tube 400, and the waste liquid chamber is connected to the other end of the tube 400 to allow the solution discharged through the tube 400 to be introduced into the waste liquid chamber.

Then, 100 µl of a solution containing a plurality of magnetic beads b having a diameter of 4.6 µm was introduced into the channel 110 through the in-let 111. Next, after the driving device 500 moved the magnetic body 200 to the first position to cause agglomeration of the magnetic beads b, the solution accommodated in the channel 110 was air-washed by using a pipette, and as a result, only a plurality of magnetic beads b agglomerated by the magnetic body 200 remained in the channel 110.

Next, a solution containing lysis buffer:blood:a proteinase K solution: 40% IPA at a ratio of 40 µl:40 µl:8 µl:20 µl was introduced through the in-let 111, and ultrasonic energy of (1) 0.6 MHz to 0.8 MHz, (2) 0.8 MHz to 1.0 MHz, (3) 1.0 MHz to 1.2 MHz, and (4) 1.2 MHz to 1.4 MHz was transmitted to the chip 100 by operating the function generator 600, and the degree of dispersion of the magnetic beads b was observed after 20 seconds.

Figure 7A:
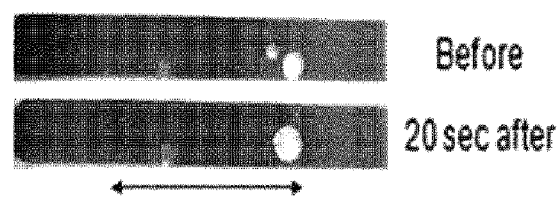
FIG. 7A to 7D show experimental results of the Verification Experiment 3 for verifying the superiority of the frequency bandwidth of ultrasound energy applied to a chip 100 by using the apparatus and the method for extracting genome according to an embodiment of the present disclosure.
Figure 7B:
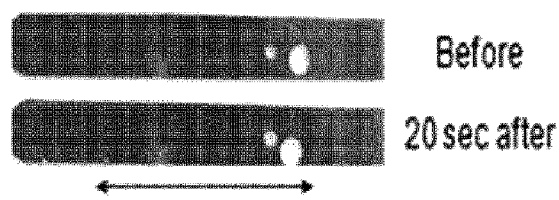
Figure 7C:
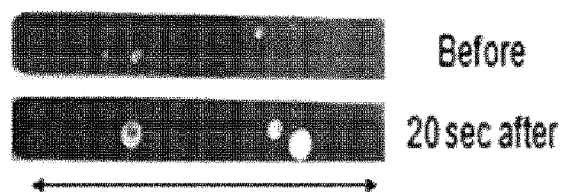
Figure 7D:
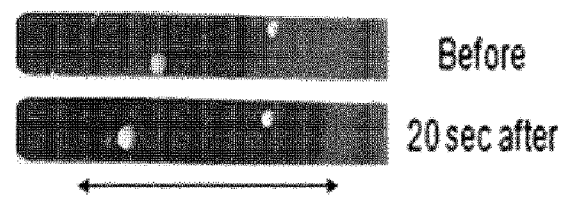

The result of the experiment confirmed that the degree of dispersion of the magnetic beads b was greatest when the ultrasound energy in the (3) 1.0 MHz to 1.2 MHz bandwidth was applied to the chip 100 (FIG. 7C).

The greater degree of dispersion of the magnetic beads b means a larger amount of DNA adsorbed to the magnetic beads b, and thus, this means an increased yield of DNA. Therefore, it was confirmed that the apparatus for extracting genome according to the present disclosure can achieve the highest yield of DNA when ultrasound energy having the 1.0 MHz to 1.2 MHz bandwidth is applied to the chip 100.

6. Verification Experiment 4

The verification experiment was conducted to find the optimum pattern of ultrasound energy transmitted to the chip 100 by the ultrasound transducer 300 (FIG. 8A to 8D).

First, the out-let 115 of the channel 110 is connected to the tube 400, and the waste liquid chamber is connected to the other end of the tube 400 to allow the solution discharged through the tube 400 to be introduced into the waste liquid chamber.

Then, 100 µl of a solution containing a plurality of magnetic beads b having a diameter of 4.6 µm was introduced into the channel 110 through the in-let 111. Next, after the driving device 500 moved the magnetic body 200 to the first position to cause agglomeration of the magnetic beads b, the solution accommodated in the channel 110 was air-washed by using a pipette, and as a result, only a plurality of magnetic beads b agglomerated by the magnetic body 200 remained in the channel 110.

Next, a solution containing lysis buffer:blood:a proteinase K solution: 40% IPA at a ratio of 40 µl:40 µl:8 µl:20 µl was introduced through the in-let 111, by operating the function generator 600, the ultrasound energy was transferred to the chip 100 with the following patterns: (1) pattern having a slope of 0.02 MHz/sec from 1.0 MHz to 1.2 MHz in which the frequency increases for 10 seconds, and having a slope of −0.02 MHz/sec from 1.2 MHz to 1.0 MHz in which the frequency decreases for 10 seconds ('Slope'); (2) pattern having a slope of 0.2 MHz/sec from 1.0 MHz to 1.2 MHz, in which the frequency increase pattern is repeated for 20 seconds ('Pulse'); and (3) pattern having a slope of 2.0 MHz/sec from 1.0 MHz to 1.2 MHz, in which the frequency increase pattern is repeated for 20 seconds ('Vibration'), and then the yield of DNA was compared.

Figure 8A:
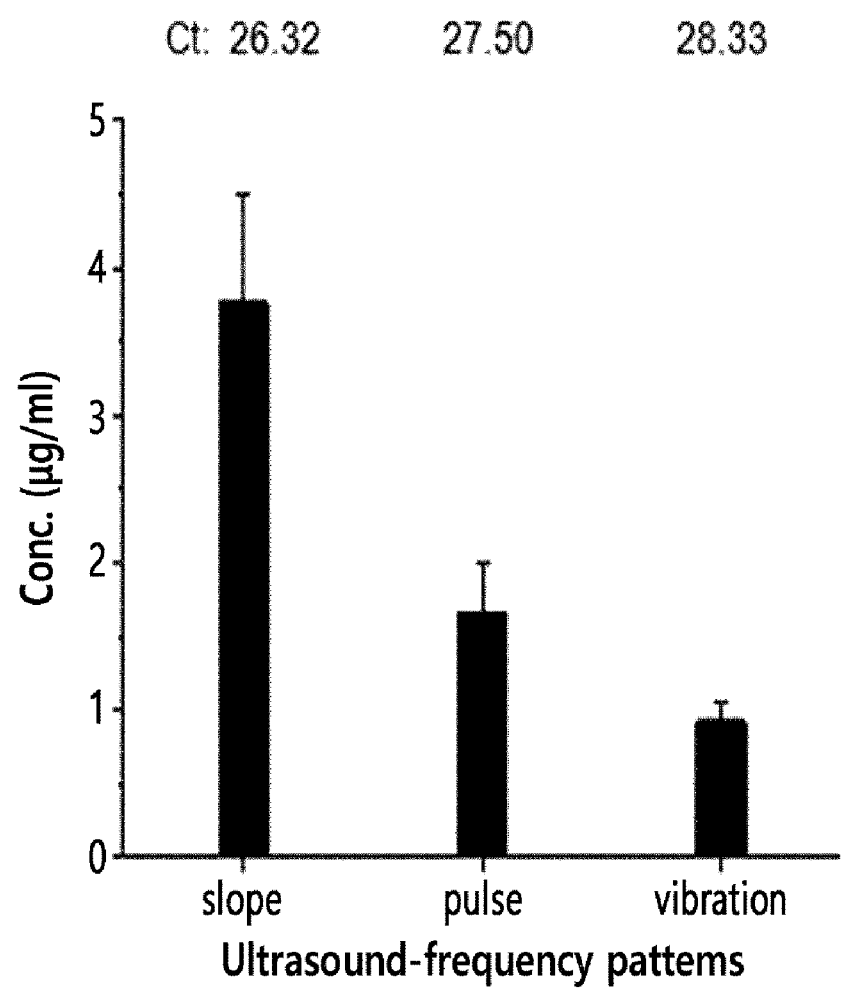
Figure 8B:
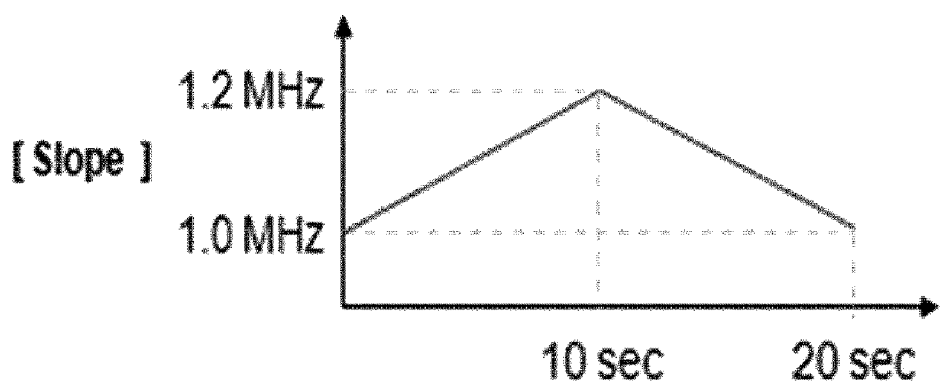
Figure 8C:
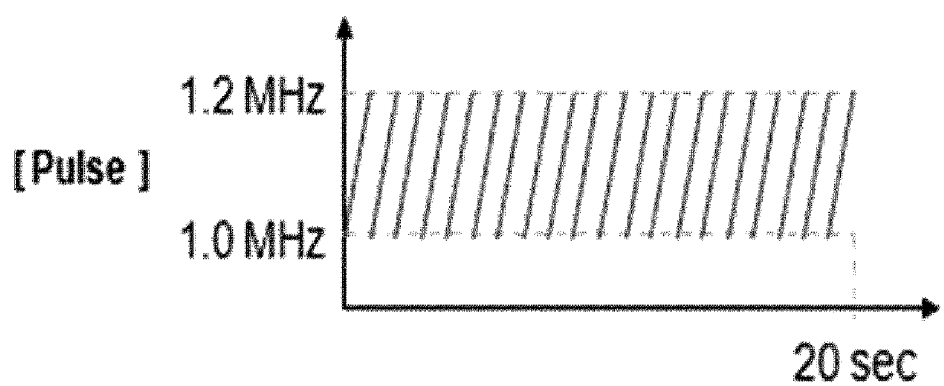

The result of the experiment showed that the yield of DNA of about 4 µg/ml was obtained with the (1) 'Slope' pattern, which proved that a higher yield can be achieved than about 1.7 µg/ml ('Pulse') and about 1.0 µg/ml ('Vibration') results of using the other patterns (FIG. 8A).

It will be apparent to those skilled in the art that various modifications and variations can be made to the present disclosure without departing from the spirit and scope of the present disclosure as defined by the following claims and their equivalents. Accordingly, the scope of protection of the present disclosure should be determined by the claims.

DESCRIPTION OF THE REFERENCE NUMERALS

100: Chip
110: Channel
111: In-let
112: Passage channel
113: Reaction channel
114: Discharge channel
115: Out-let
200: Magnetic body
300: Ultrasound transducer
400: Tube
500: Driving device
600: Function generator 700 Amplifier
800: Controller

What is claimed is:
1. A method for extracting genome, comprising:
(a) introducing a solution containing a plurality of magnetic beads into a channel;
(b) moving a magnetic body to a first position with respect to the channel to cause agglomeration of the plurality of magnetic beads, and discharging the solution excluding the plurality of magnetic beads to outside of the channel after the step (a);
(c) introducing a solution containing a lysis buffer and a target sample into the channel after the step (b); and
(d) moving the magnetic body to a second position with respect to the channel, and then applying ultrasound energy of a predetermined pattern to the channel after the step (c), wherein the plurality of magnetic beads is collided against a substance contained in the target sample so that the substance is lysed, and
target genome contained in the substance is eluted and adsorbed to the plurality of magnetic beads, and
wherein a distance between the magnetic body and the channel in the first position is shorter than in the second position,
wherein the predetermined pattern of the ultrasound energy comprises:
a first pattern having a predetermined voltage for a predetermined first time period, wherein frequency linearly increases from a first frequency to a second frequency;
after the first pattern, a second pattern having the predetermined voltage for a time period of which duration is the same with the predetermined first time period, wherein the frequency linearly decreases from the second frequency to the first frequency;
after the second pattern, a third pattern having the predetermined voltage for a predetermined second time period, in which the ultrasound energy is not applied;
after the third pattern, a fourth pattern having the predetermined voltage for a time period of which duration is the same with the predetermined first time period, wherein the frequency linearly increases from the first frequency to the second frequency; and
after the fourth pattern, a fifth pattern having the predetermined voltage for a time period of which duration is the same with the predetermined first time period, wherein the frequency linearly decreases from the second frequency to the first frequency, wherein the second frequency is higher than the first frequency,
wherein, when the predetermined pattern is the first pattern, the second pattern, the fourth pattern and the fifth pattern, the magnetic body is located in the second position, and
when the predetermined pattern is the third pattern, the magnetic body is located in the first position,
wherein at a start time of the first pattern and at a start time of the fourth pattern the magnetic beads are in an agglomerated state,
wherein the step (d) is performed without introducing a washing buffer into the channel.
2. The method for extracting genome according to claim 1, further comprising, after the step (d):
(e) moving the magnetic body to the first position to cause agglomeration of the plurality of magnetic beads to which the target genome is adsorbed, discharging the solution excluding the plurality of magnetic beads to which the target genome is adsorbed to the outside of the channel, and introducing the washing buffer into the channel; and
(f) moving the magnetic body to the second position and applying the ultrasound energy of the predetermined pattern to the channel.
3. The method for extracting genome according to claim 2, further comprising, after the step (f):
(g) moving the magnetic body to the first position to cause agglomeration of the plurality of magnetic beads to which the target genome is adsorbed, discharging the solution excluding the plurality of magnetic beads to which the target genome adsorbed to the outside of the channel, and introducing an elution solution for separating the target genome from the plurality of magnetic beads into the channel; and
(h) moving the magnetic body to the second position and applying the ultrasound energy of the predetermined pattern to the channel.
4. The method for extracting genome according to claim 3, wherein the ultrasound energy of the predetermined pattern is applied to the channel for a predetermined number of times or more in steps (d), (h), and (f).
5. The method for extracting genome according to claim 3, further comprising, after the step (h),
(i) moving the magnetic body to the first position to cause agglomeration of the plurality of magnetic beads.
6. The method for extracting genome according to claim 1, wherein the target sample is blood.
7. The method for extracting genome according to claim 1, wherein the substance colliding against the plurality of magnetic beads is leukocyte, and the target genome is DNA or RNA.
8. The method for extracting genome according to claim 1, wherein the first frequency is in the range of 0.95 MHz to 1.05 MHz,
the second frequency is in the range of 1.14 MHz to 1.26 MHz, and
the predetermined voltage is in the range of 270 mV to 330 mV.
9. The method for extracting genome according to claim 1, wherein the predetermined first time period is in the range of 9 to 11 seconds, and the predetermined second time period is in the range of 36 to 44 seconds.

* * * * *